United States Patent
Coffey et al.

(10) Patent No.: US 6,599,246 B1
(45) Date of Patent: Jul. 29, 2003

(54) APPARATUS AND METHOD FOR SUBSTANTIALLY STATIONARY TRANSDUCER THERAPEUTIC ULTRASOUND TREATMENT

(76) Inventors: Kenneth W. Coffey, 134 E. 18th St., Unit C, Tulsa, OK (US) 74119; Gregory F. Dorholt, 7020 S. Jamestown, Tulsa, OK (US) 74136

( * ) Notice: Subject to any disclaimer, the term of this patent is extended or adjusted under 35 U.S.C. 154(b) by 41 days.

(21) Appl. No.: 10/055,764

(22) Filed: Jan. 25, 2002

(51) Int. Cl.7 .................................................. A61B 8/00
(52) U.S. Cl. ...................................................... 600/437
(58) Field of Search ................................ 600/437, 439, 600/438, 443, 447; 601/2, 3; 604/20, 45

(56) References Cited

U.S. PATENT DOCUMENTS

| | | | |
|---|---|---|---|
| 5,989,208 A | * 11/1999 | Nita | 604/22 |
| 6,428,477 B1 | * 8/2002 | Mason | 600/437 |
| 6,488,626 B1 | * 12/2002 | Lizzi et al. | 600/437 |

* cited by examiner

Primary Examiner—Francis J. Jaworski
Assistant Examiner—Maulin Patel
(74) Attorney, Agent, or Firm—Frank L. Hart

(57) ABSTRACT

An apparatus and method for therapeutic ultrasound treatment using a plurality of spaced apart piezoelectric crystals sequentially activated for a preselected time, thereby allowing the transducer containing the piezoelectric crystals to be used substantially stationary relative to the area being treated.

16 Claims, 2 Drawing Sheets

APPARATUS AND METHOD FOR SUBSTANTIALLY STATIONARY TRANSDUCER THERAPEUTIC ULTRASOUND TREATMENT

TECHNICAL FIELD

The subject invention relates to apparatus and the method of using same for therapeutic ultrasound treatment. More particularly, the subject invention is directed to an apparatus and method of using same for the therapeutic ultrasound treatment during which the transducer is maintained substantially stationary relative to the area being treated.

BACKGROUND ART

Ultrasound has been employed in medicine for more than 50 years. The application of ultrasound for medical treatment was introduced in Germany in the late 1930s, and in the United States in the late 1940s.

Sound with a frequency greater than 20,000 Hz is called ultrasound. For a given sound source, the higher the frequency, the less the emerging sound beam diverges. Sound at audible frequencies appears to spread out in all directions, whereas ultrasound beams are well collimated, similar to a light beam leaving a flashlight. Ultrasound beams at frequencies greater than 800 kHz are sufficiently collimated to selectively expose a limited target area for physical therapy treatment. At frequencies less than about 800 kHz the ultrasound beam's intensity is sufficiently low as to be outside the range for physical therapy treatment, but has been used at these low intensity levels for diagnostic procedures.

Absorption of sound, and therefore attenuation, increases as the frequency increases. Absorption occurs in part because of the internal friction in tissue that needs to be overcome in the passage of sound. The higher the frequency, the more rapidly the molecules are forced to move against this friction. As the absorption increases, there is less sound energy available to propagate through the tissue. At frequencies greater than 20 MHz, superficial absorption becomes so great that less than 1 percent of the sound penetrates beyond the first centimeter.

Therefore, for physical therapy applications, the frequency range is generally considered to be limited to frequencies within the range of about 800 kHz to about 3.3 MHz. Frequently most often used for physical therapy application is a frequency of about 1.0 MHz or 3.0 MHz because they offer a good compromises between sufficiently deep penetration and adequate heating under customary exposure levels.

Sound waves can be produced as continuous wave or as pulsed wave. A pulsed wave is intermittently interrupted. Pulsed waves are further characterized by specifying the fraction of time the sound is present over one pulse period. This fraction is called the duty cycle and is calculated by dividing the pulse time on by the total time of a pulse period; e.g. time on plus time off. Duty cycles for therapy machines, when in the pulsed mode, range from about 5 per cent to about 50 percent.

The strength of an ultrasound beam is determined by its intensity. Intensity is the rate at which energy is delivered per unit area. It is expressed in units of watts per square centimeter. Intensities employed in physical therapy are limited to the range of about 0.25 to about 3.00 watts per square centimeter.

Where sound beams are pulsed, the intensity of the beam will be zero when the sound beam is off and at its maximum during the pulse. The temporal average intensity of a beam is obtained by averaging the intensity over both the on and off periods. The amount of heating depends on the temporal average intensity. The temporal average intensity is decreased proportionally to the amount of time the sound is off. Thus less heating will occur even though the temporal peak intensity is unchanged.

Because the ultrasound beam is not uniform, some regions of the beam will be more intense than other regions. The measurement of intensity gives an average intensity and is referred to as the spatial average intensity. The World Health Organization limits the spatial average intensity to a maximum of 3 watt per square centimeter. Intensities greater than 10 watt per square centimeter are used to destroy tissue surgically and intensities (temporal average) below 0.21 watt per square centimeter are used for diagnostic purposes.

Therapeutic ultrasound treatment is customarily performed using a moving transducer technique with a small layer of gel or lotion between the transducer and the tissue. This movement is to avoid damage caused by beam "hot spots" as is known in the industry and in general to treat areas which are typically larger than the area of the transducer.

Ultrasound treatment is an attended therapy that requires a clinician to be present to move the sound head over the treatment area. This movement of the transducer over the gel covering the treatment area causes the gel to be displaced and therefore requires constant attended application of the gel.

Movement speed rate of the transducer during treatment vary widely from one clinician to another. Therefore, there often is misuse of the treating machine, by the clinician which is caused by moving the transducer too fast, not using enough coupling medium, not moving the transducer, trying to treat too large and area, not keeping the transducer in contact with the patient and other faults.

Since treatments must be supervised by a clinician, the patient is often limited to specific treatment times with greater repetitions. It has been found that often it would be more beneficial to the patient to have fewer treatments each of longer duration.

The present invention is directed to over come one or more of the heretofore problems, as set forth above.

DISCLOSURE OF THE INVENTION

In one aspect of the invention, a therapeutic ultrasound system is adapted to substantially stationary transducer application during use. The system has a first means for generating a pulsed digital signal at a frequency in the range of greater than about 800 kHz to less than about 3.0 MHz and a spatial average intensity in the range of about 0.1 watt per square centimeter to about 3.0 watt per square centimeter.

A sine wave filter is connected to the first means and is adapted to receive the signal form the first means and convert it to a second signal. A programmable controlling element is connected to the sine wave filter and is adapted to deliver said second signal to a plurality of separate locations in a preselected sequence, each for a preselected period of time.

A transducer has a plurality of spaced apart piezoelectric crystals each operatively connected to the programmable controlling element for sequentially receiving the second signal and delivering a pulsed sound beam therefrom. Means is provided for maintaining the transducer substantially stationary during operation thereof.

In another aspect of the invention, a method of therapeutic ultrasound treatment is provided. A pulsed digital signal is generated at a frequency in the range of greater than about 800 kHz to less than about 3.0 MHz and a spatial average intensity in the range of about 0.1 watt per square centimeter to about 3.0 watt per square centimeter. The signal is converted to a pulsed sine wave signal. The pulsed sine wave signal is delivered to a first plurality of separate locations in a preselected sequence, each for a preselected time period. The pulsed sine wave signal is received at said first plurality of separate locations and ultrasound energy is delivered outwardly from each of said separate locations while maintaining the first plurality of separate locations substantially stationary relative to a first area being treated. Means is provided for maintaining the transducer substantially stationary during operation thereof.

BEST MODE FOR CARRYING OUT THE INVENTION

Figure 1:
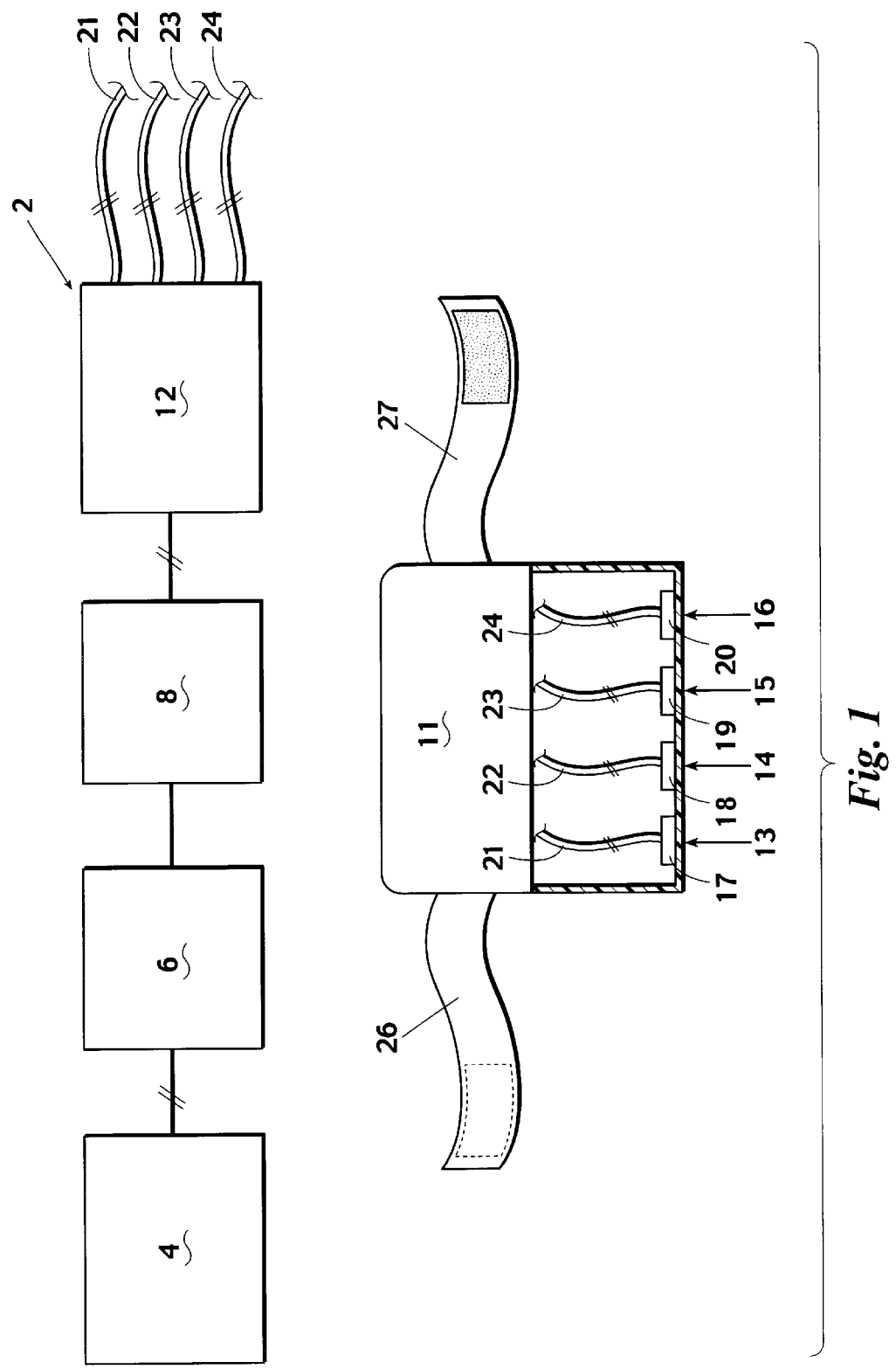
FIG. 1 is a diagrammatic view of the apparatus of this invention.

Referring to FIG. 1, a Therapeutic ultrasound system 2 is shown. The ultrasound system 2 has an oscillator 4 connected to a variable gain transformer 6 which is connected to a sine wave filter 8 for converting a pulsed digital signal to a pulsed sine wave signal. The pulsed sine wave signal is delivered by line 10 to a programmable controlling element 12.

The oscillator 4 and variable gain transformer 6 are adapted to generating a pulsed digital signal at a frequency in the range of greater than about 800 kHz to less than about 3.0 MHz and a spatial average intensity in the range of about 0.1 watt per square centimeter to about 3.0 watt per square centimeter, preferably about 1.0 watt per square centimeter. At these values, the therapeutic ultrasound system 2 intensity is limited to the values used for therapeutic treatment.

The programmable controlling element 12 receives the pulsed sine wave signal via line 10 and delivers said signal to a plurality of separate locations 13–16 within a transducer 11, each location 13–16 which is occupied by a separate piezoelectric crystals 17–20, via respective lines 21–24. The piezoelectric crystals 17–20 receives the pulsed sine wave signal in a preselected sequence, each for a preselected time period as delivered from the controlling element 12.

In response to pulsed actuation, each piezoelectric crystal 17–20 delivers ultrasound energy outwardly from the transducer 11. Since each individual piezoelectric crystal 17–20 is actuated to deliver ultrasound energy during only a fraction of the total time of one complete cycle of operation of the transducer 11 and since the individual piezoelectric crystals 17–20 are spaced one from the other, the transducer 11 can remain stationary relative to the area being treated without the development of undesirable "hot spots" as described above. For this reason, the transducer 13 can be strapped to an individual by, for example by a Velcro strap 26, Velcro straps 26, 27, or any other means for maintaining the transducer 11 stationary relative to the area being ultrasonically treated.

The oscillator is controllable to maintain the duty cycle of the pulsed signal in the range of about 5 percent to about 50 percent. Preferably the duty cycle is maintained at about 20 percent. Maintaining a low duty cycle percentage coupled with sequencing of multiple piezoelectric elements assures against the avoidance of "hot spots" in an immobile transducer.

The lines 21–24 which connect the transducer 11 to the controlling element are preferably coaxial cables. The purpose of the coaxial cable is to maximize transmission of the electrical energy and to minimize frequency distortion and interference with the external environment.

Figure 2:
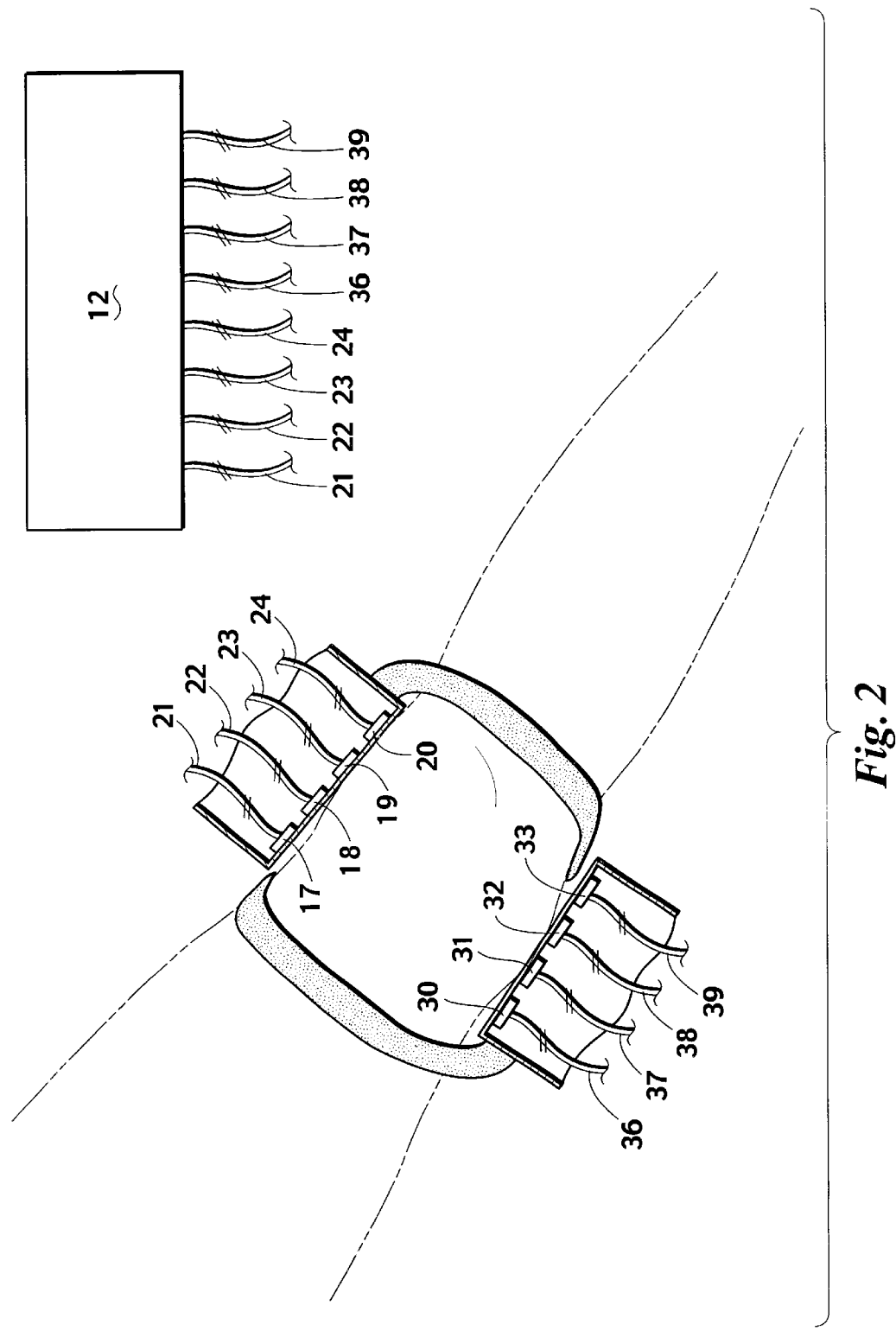
FIG. 2 is a diagrammatic view of the apparatus of this invention which has a second transducer.

Referring to FIG. 2, another embodiment of the invention is shown, which has a plurality of transducers 11, 28, each having a plurality of separate piezoelectric crystals 17–20, 30–33. In this embodiment each transducer has a separate group of piezoelectric crystals with each crystal group 17–20, 30–33 connected to the controlling element 12 and each crystal group is independently sequenced relative to the other crystal group.

Each of the transducers 11, 28 are operational during the same period. FIG. 2 shows such a use where a separate transducer 11, 28 is treating a respective opposed side of a patients knee.

The ultrasound generator preferred in this invention is part No. 0185, available from Rich-Mar Corporation, PO Box 879, Inola, Okla. 74036, Phone 918-543-2222. The transducer 11 or 28 will also be available as an off-the-shelf item from Rich-Mar Corporation, as will be the programmable controlling element 12. However, it is urged that one skilled in the art, after reading this specification can easily build the apparatus of this invention without employing actions of an inventive nature.

Industrial Applicability

In the method of using the apparatus of this invention, a pulsed digital signal is generated at a frequency in the range of greater than about 800 kHz to less than about 3.0 MHz and a spatial average intensity in the range of about 0.1 watt per square centimeter to about 3.0 watt per square centimeter. This generated signal is then converted to a pulsed sign wave signal which is delivered to a first plurality of separate locations in a preselected sequence, each for a preselected period of time. The signal is received sequentially at each of said first plurality of separate locations and result in the delivery of ultrasound energy outwardly from each of said separate locations while maintaining the first plurality of separate locations substantially stationary relative to a first area being treated.

FIG. 2 shows another method having two transducers 11,28 connected to the controlling element 12, each transducer 11,28 being functionally similar. The second transducer 28 has a second plurality of separate locations operatively separate and spaced from said first plurality of separate locations and adapted to deliver ultrasound energy outwardly therefrom while maintaining the second plurality of separate locations substantially stationary relative to a different second area being treated. This other embodiment of the invention is most useful in treating a joint of an individual which sustained damage to opposed sides of the joint.

Other aspects, objects and advantages of this invention can be obtained from a study of the drawings, the disclosure and the appended claims.

What is claimed is:

1. A therapeutic ultrasound system adapted to substantially stationary transducer application, comprising:

first means for generating a pulsed digital signal at a frequency in the range of greater than about 800 kHz to less than about 3.0 MHz and a spatial average intensity in the range of about 0.1 watt per square centimeter to about 3.0 watt per square centimeter;

a sine wave filter connected to the first means and adapted to receive the signal from the first means and converting it to a second signal;

a programmable controlling element connected to the sine wave filter and being adapted to deliver said second signal to a plurality of separate locations in a preselected sequence, each for a preselected period of time;

a transducer having a plurality of spaced apart piezoelectric crystals each operatively connected to the programmable controlling element for sequentially receiving the second signal and delivering a pulsed ultrasound energy outwardly therefrom; and means for maintaining the transducer substantially stationary during operation thereof.

2. A system, as set forth in claim 1, wherein the first means includes an oscillator connected to a variable gain transformer, said oscillator being controllably interrupted to produce a signal having a preselected duty cycle.

3. A system, as set forth in claim 2, wherein said oscillator is controllable to maintain the duty cycle of the pulsed signal in the range of about 5 percent to about 50 percent.

4. A system, as set forth in claim 1, wherein the piezoelectric crystals of the transducer are each connected to the programmable controlling element via a respective coaxial cable.

5. A system, as set forth in claim 1, wherein the spatial average intensity of system is maintainable at about 1 watt per square centimeter.

6. A system, as set forth in claim 1, wherein there are at least 4 piezoelectric crystals each being actuateable only one preselected time period during a sequencing cycle of the programmable controlling element.

7. A system, as set forth in claim 1, wherein there are a plurality of groups of piezoelectric crystals with each piezoelectric group comprising a plurality of separate piezoelectric crystals.

8. A system, as set forth in claim 7, wherein each piezoelectric crystal group is independently and separately controlled relative to other piezoelectric crystal groups of the system.

9. A system, as set forth in claim 1, including means for maintaining the transducer substantially stationary relative to a preselected location on a user.

10. A system, as set forth in claim 9, wherein the maintaining means is at least one Velcro strap, said strap having a length sufficient to encircle a portion of a user's body.

11. A system, as set forth in claim 9, wherein the maintaining means are a plurality of Velcro straps.

12. A system, as set forth in claim 1, including a plurality of separate transducers each having a plurality of spaced apart piezoelectric crystals each operatively connected to the programmable controlling element for sequentially receiving the second signal therefrom.

13. A system, as set forth in claim 12, wherein the piezoelectric crystals of one of the separate transducers are independently sequenced relative to the sequence of operation of the piezoelectric crystals of the other transducer.

14. A system, as set forth in claim 13, wherein each of the transducers are operational during the same period.

15. A method of therapeutic ultrasound treatment, comprising:

generating a pulsed digital signal at a frequency in the range of greater than about 800 kHz to less than about 3.0 MHz; and a spatial average intensity in the range of about 0.1 watt per square centimeter to about 3.0 watt per square centimeter;

converting the pulsed digital signal to a pulsed sine wave signal;

delivering the pulsed sine wave signal to a first plurality of separate locations in a preselected sequence, each for a preselected period of time; and receiving the pulsed sine wave signal at said first plurality of separate locations and delivering ultrasound energy outwardly from each of said separate locations while maintaining the first plurality of separate locations substantially stationary relative to a first area being treated.

16. A method, as set forth in claim 15, including a second plurality of separate locations operatively separate and spaced from said first plurality of separate locations and adapted to deliver ultrasound energy outwardly therefrom while maintaining the second plurality of separate locations substantially stationary relative to a different second area being treated.

* * * * *